United States Patent [19]

Green

[11] Patent Number: 4,503,178
[45] Date of Patent: Mar. 5, 1985

[54] CYCLIC PHOSPHINE OXIDES AND THEIR USE AS FLAME RETARDANTS IN STYRENE MODIFIED POLYPHENYLENE ETHER RESINS

[75] Inventor: Joseph Green, East Brunswick, N.J.

[73] Assignee: FMC Corporation, Philadelphia, Pa.

[21] Appl. No.: 604,254

[22] Filed: Apr. 26, 1984

[51] Int. Cl.³ .................. C08K 5/53; C07D 105/02
[52] U.S. Cl. .................... 524/116; 524/129; 525/132; 568/12
[58] Field of Search ............... 524/116, 129; 525/132; 568/12

[56] References Cited

U.S. PATENT DOCUMENTS

| | | | |
|---|---|---|---|
| 3,257,357 | 6/1966 | Stamatoff | 528/215 |
| 3,257,358 | 6/1966 | Stamatoff | 528/215 |
| 3,306,874 | 2/1967 | Hay | 528/215 |
| 3,306,875 | 2/1967 | Hay | 528/215 |
| 3,400,163 | 9/1968 | Mason et al. | 568/12 |
| 3,502,730 | 3/1970 | Mason et al. | 568/12 |
| 3,639,506 | 2/1972 | Haaf | 524/120 |
| 3,917,560 | 11/1975 | Hoffman | 524/129 |
| 4,154,775 | 5/1979 | Axelrod | 524/120 |
| 4,163,760 | 8/1979 | Elsner et al. | 568/12 |
| 4,255,324 | 3/1981 | Granzow et al. | 524/129 |
| 4,287,119 | 9/1981 | Braksmayer et al. | 524/139 |

Primary Examiner—John Kight
Assistant Examiner—Kriellion Morgan
Attorney, Agent, or Firm—Robert D. Jackson; Eugene G. Horsky; Eugene G. Seems

[57] ABSTRACT

Cyclic phosphine oxides of the formula:

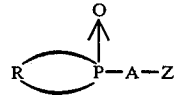

wherein P is phosphorus, O is oxygen, A is an alkylene chain of 2 to 12 carbon atoms, Z is a polar group and R represents the carbon atoms in a phosphorus-containing ring formed by alkylating an ethylenically unsaturated cyclic hydrocarbon with phosphine.

The cyclic phosphine oxides are useful as flame retardants for styrene modified polyphenylene ether resins.

18 Claims, No Drawings

CYCLIC PHOSPHINE OXIDES AND THEIR USE AS FLAME RETARDANTS IN STYRENE MODIFIED POLYPHENYLENE ETHER RESINS

This invention relates to phosphine oxides and in particular to certain novel cyclic phosphine oxides as flame retardants in polyphenylene ether resins.

The polyphenylene ethers are a well-known class of linear thermoplastic engineering resins, the description and preparation of which are documented at length in the technical and patent literature; see U.S. Pat. Nos. 3,306,874 and 3,306,875 to Hay and U.S. Pat. Nos. 3,257,357 and 3,257,358 to Stamatoff. Generally speaking, polyphenylene ethers are combined with other polymers such as a polystyrene to provide modified polyphenylene ether resins. An important commercial grade polyphenylene ether engineering plastic contains about 35 to 85% by weight polyphenylene ether and about 55 to 15% by weight of a polystyrene resin. Such modified polyphenylene ether resins, with which the present invention is particularly concerned, are used extensively in the automotive and transportation industries as a replacement for metal to reduce vehicle weight. Makers of electrical/electronic equipment and appliances also use substantial quantities of such resins.

Styrene modified polyphenylene ether resins will burn if subjected to flame. To reduce their combustibility, such resins are formulated with a flame retardant additive of which a large number have been described. One well-known flame retardant is a blend of an aromatic halogen compound and an aromatic phosphate as disclosed in U.S. Pat. No. 3,639,506. A preferred composition in accordance with that teaching comprises from 20 to 80% by weight of poly(2,6-dimethyl-1,4-phenylene ether, 20 to 80% by weight of a high impact polystyrene (styrene modified with rubber) and from 3 to 25 parts by weight per 100 parts by weight of the polyphenylene ether composition of a flame retardant combination of 1 part triphenyl phosphate and 3 to 4 parts of a heavily chlorinated biphenyl. U.S. Pat. No. 4,154,775 states that cyclic phosphates are, by themselves, an effective, non-plasticizing flame retardant additive for polyphenylene ether resins. Numerous other organic phosphates have been proposed and tested as flame retardants.

An improved class of fire retardant compounds for polyphenylene ether compositions are certain 3-hydroxyalkyl phosphine oxides disclosed in applicant's U.S. Pat. No. 4,287,119. These compounds can be represented by the formula:

$$(HO-CH_2CHCH_2)_{(3-n)} \overset{R_1}{\underset{}{P}} (R_2)_n \overset{O}{\underset{}{\parallel}}$$

wherein $R_1$ is selected from the group consisting of hydrogen and methyl radicals, $R_2$ is an alkyl radical of 4 to 8 carbon atoms and n is either zero or one.

There are numerous problems associated with the development of a satisfactory flame retardant for plastics. In addition to its flame suppressing capacity, the flame retardant must be heat and light stable, noncorrosive, nontoxic, compatible, and not adversely alter the mechanical properties of the plastic.

One type of physical deformation that occurs in flame retardant thermoplastic resins, such as the polyphenylene ether compositions or resins mentioned herein, is known as stress cracking. Commonly referred to as juicing in the trade, the flame retardant boils off or exudes during hot molding of the resin and condenses on the mold and the surface of the resin. The plastic part may be under stress as a result of the molding and the condensed flame retardant may result in cracking of the molded part. Failure can occur during molding or on storage of the final manufactured resin.

Stress cracking is particularly difficult to control when using organic phosphates as a flame retardant in styrene modified polyphenylene ether resins; juicing can be quite severe. Much less prone to cause stress cracking are the aforementioned hydroxyalkylphosphine oxides. These are generally excellent flame retardant additives although their thermal stability and ease of incorporation into the resin are not as good as might be desired. Volatility can also be a factor with some of the lower boiling members.

It has now been discovered that flame retardant styrene/polyphenylene ether polymer compositions, which are highly resistant to stress cracking, can be realized by using as the flame retardant agent therein certain novel cyclic phosphine oxides.

The herein novel cyclic phosphine oxides are the product of a three-step synthesis in which the first step is carried out by alkylating phosphine in the presence of a free radical source with an ethylenically unsaturated cyclic hydrocarbon of the formula:

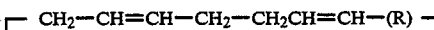

$$CH_2-CH=CH-CH_2-CH_2CH=CH-(R)$$

wherein R is $-CH_2-$, $-CH_2CH_2CH_2-$ or $-CH_2CH_2CH=CHCH_2-$ to produce a cyclic phosphine containing secondary phosphine groups, >PH as part of the cyclic phosphine ring structure. The so obtained part of the cyclic phosphine ring structure is then further alkylated with a 1-alkene having at least one polar group, preferably terminal to the double bond, whereby residual phosphine hydrogen atoms are replaced by an alkyl radical containing the said polar group. This alkylated phosphine is then oxidized to the corresponding oxide.

The aforedescribed reaction can be illustrated by the scheme set forth below in which the ethylenically unsaturated cyclic hydrocarbon is cyclooctadiene.

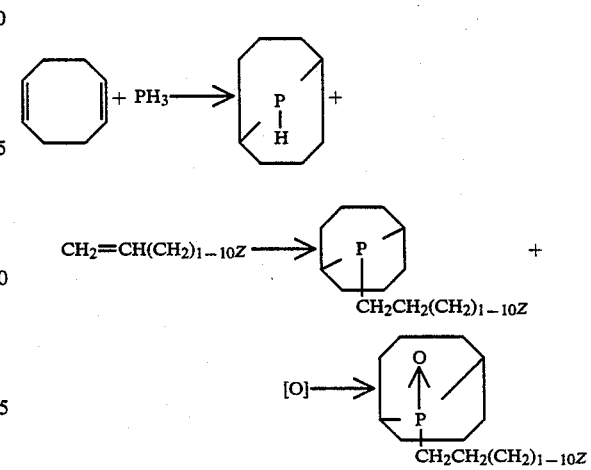

wherein Z is a polar group as defined heretofore. Phosphine and cyclooctadiene may also react to form other phosphine structures such as:

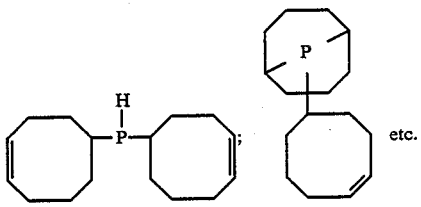

The presence of these by-product phosphines in the reaction mixture can result in other oxidized phosphine derivatives being formed including phosphine oxides and phosphinic acids.

The cyclic phosphine oxides of the invention can be characterized by the presence of the following configuration:

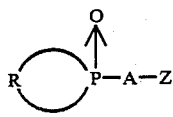

in which P is phosphorus, O is oxygen, A is an alkylene chain of 2 to 12 carbon atoms, Z is a polar group such as amino, hydroxy, cyano, amide, carboxylic acid and esters thereof, sulfonic acid and esters thereof and R represents the number of carbon atoms in a phosphorus-containing ring formed when alkylating phosphine with the herein ethylenically unsaturated cyclic hydrocarbons.

Exemplary ethylenically unsaturated cyclic hydrocarbons used as intermediates herein include cyclooctadiene, cyclodecadiene and cyclododecatriene.

Some exemplary 1-alkenes containing a polar group are set forth in the following list:

$CH_2=CH-CH_2CONH_2$
$CH_2=CH-CH_2CONHCH_3$
$CH_2=CH-CH_2OH$
$CH_2=CH-CH_2CH_2CH_2OH$
$CH_2=CH-CH_2CH_2NH_2$
$CH_2=CH-CH_2CH_2NHC_2H_5$
$CH_2=CH-CH_2CH_2COOC_2H_5$
$CH_2=CH-CH_2NH_2$
$CH_2=CH-CH_2SO_2OC_2H_5$ $$CH_2=CHCHCH_2CH_2OH \atop {\overset{|}{CH_3}}$$

$CH_2=CHCH_2CONHCH_2NHCOCH_2CH=CH_2$ $$CH_2=CH-\overset{\overset{C_2H_5}{|}}{\underset{\underset{H}{|}}{C}}CONH_2$$

$CH_2=CH-CH_2COOC_4H_9$
$CH_2=CH-CN$
$CH_2=CH-COOH$
$CH_2=CH-CONH_2$
$CH_x=CH-COOCH_3$
$CH_2=CH-COOR$ $$CH_2=\overset{\overset{|}{}}{\underset{\underset{CH_3}{|}}{C}}-COOR$$

$$CH_2=CH-CH_2NH \atop {\overset{|}{R}}$$

R = cyclohexyl

Free radical-yielding catalysts, suitable for use in the present reaction, are known entities and include peroxidic radical-forming agents or azobisisobutyronitrile.

In preparing the cyclic phosphine oxides of the invention, the cyclic phosphine starting materials are formed in the known manner by reacting an ethylenically unsaturated cyclic hydrocarbon with phosphine in the presence of the radical-producing catalyst, preferably azobisisobutyronitrile. The reaction is conducted at moderately elevated temperatures, 100° C. being a practical and working temperature. It is preferred to carry out the reaction in a relatively inert, normally liquid organic solvent of which the aromatic hydrocarbons such as toluene or xylene are suitable. The proportions of unsaturated cyclic hydrocarbon to phosphine are selected in order that the resulting cyclic phosphine will contain some free phosphine hydrogens. Thus, using approximately molar amounts of phosphine and cyclooctadiene results in a cyclic phosphine having secondary phosphine groups >PH as shown in the following formula:

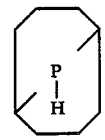

The cyclic phosphine is then alkylated under free radical generating conditions with the 1-alkene, bearing a polar group, to give a tertiary phosphine which on oxidation, preferably with hydrogen peroxide, results in a cyclic phosphine oxide of the type herein. Using such exemplary 1-alkenes as acrylic acid, allyl alcohol, acrylonitrile and acrylamide, the cyclic phosphine oxide described aforesaid would have the following structure:

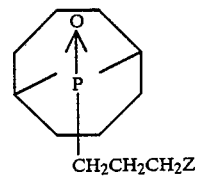

wherein Z is —OH, —NH$_2$, —CONH$_2$ or —COOH.

Reference is now made to the following examples.

EXAMPLE 1

Into a one gallon stainless steel pressure reactor is placed 500 g of toluene and 140 g (4.1 moles) of phosphine. The reaction vessel is sealed and heated to about 100° C. with stirring. A solution of 475 g (4.4 moles) of cyclooctadiene, 10 g of azobisisobutyronitrile and 341 g of toluene is added in increments over a five hour period. The reaction mixture is heated and stirred at 100° C. for an additional two hours after the last addition and then allowed to cool to room temperature.

The unreacted phosphine is vented from the reaction vessel and the vessel reheated to 100° C. A solution of 255 g (4.4 moles) of allyl alcohol and 5 g of azobisisobutyronitrile is added in 20 ml increments every 15 minutes over a period of four hours. Heating and stirring are continued at 100° C. for an additional four hours and the reaction vessel is then allowed to cool to room temperature. The reaction netted 1671 g of crude product solution.

The reaction product is heated to 193° C./ATM and then 75° C./2.5 mm Hg to remove volatile components. The residual product is a liquid weighing over 500 g.

The residual product is dissolved in an equal volume of isopropanol and oxidized with the dropwise addition of a 30% aqueous hydrogen peroxide solution diluted with an equal volume of isopropanol. When the exothermic reaction subsides, the solution of phosphine oxide is tested by adding one drop of the solution to 1 ml of carbon disulfide until no red coloration can be detected visually in the carbon disulfide layer. This indicates complete oxidation of the phosphine to the phosphine oxide.

Following oxidation with hydrogen peroxide, the solvents (water and isopropanol) are removed from the reaction product by heating to 65° C. under vacuum. The resulting viscous syrup weighs 510 g. The product has the following analyses: C61.28, 61.24; H9.29, 9.15; P14.81, 14.91.

This is an effective flame retardant when added to polyphenylene oxide compositions in amounts of 4 to 15 parts per hundred.

EXAMPLE 2

Into a one gallon stainless steel pressure reactor is placed 300 g of toluene and 475 g (4.4 moles) of cyclooctadiene. The reaction vessel is sealed and heated to about 100° C. with stirring. One hundred thirty-seven g (4.0 moles) of $PH_3$ and 8 g of azobisisobutyronitrile dissolved in 400 g of toluene are added in increments over a five hour period. The reaction mixture is heated and stirred at 100° C. for an additional four hours after the last addition and then allowed to cool to room temperature.

The unreacted phosphine is vented from the reaction vessel and the vessel reheated to 100° C. A solution of 255 g (4.4 moles) of allyl alcohol and 3 g of azobisisobutyronitrile is added over a three hour period with stirring.

Heating and stirring are continued at 100° C. for an additional four hours and the reaction vessel is then allowed to cool to room temperature. The reaction netted 1500 g of crude product solution.

Distillation and oxidation are conducted similar to that of Example 1. The resultant viscous syrup weighs about 500 g. The product has the following analyses: C63.15; 63.03; H9.75, 10.00; P14.17, 14.17.

EXAMPLE 3

Into a one gallon stainless steel pressure reactor is placed 500 g of toluene and 140 g (4.1 moles) of phosphine. The reaction vessel is sealed and heated to about 100° C. with stirrng. A solution of 475 g (4.4 moles) of cyclooctadiene, 10 g of azobisisobutyronitrile and 341 g of toluene is added in increments over a five hour period. The reaction mixture is heated and stirred at 100° C. for an additional two hours after the last addition and then allowed to cool to room temperature.

The unreacted phosphine is vented from the reaction vessel and the vessel reheated to 100° C. A solution of 240 g (4.5 moles) of acrylonitrile and 5 g of azobisisobutyronitrile and 43 g toluene is added in 20 ml increments every 15 minutes over a period of four hours. Heating and stirring are continued at 100° C. for an additional four hours and the reaction vessel is then allowed to cool to room temperature. The reaction netted 1177 g of crude product solution.

The reaction product is heated to 180° C./ATM and then 75° C./3 mm Hg to remove volatile components. The residual product is a liquid.

The residual product is dissolved in an equal volume of isopropanol and oxidized with the dropwise addition of a 30% aqueous hydrogen peroxide solution diluted with an equal volume of isopropanol. When the exothermic reaction subsides, the solution of phosphine oxide is tested by adding one drop of the solution to one ml of carbon disulfide until no red coloration can be detected visually in the carbon disulfide layer. This indicates complete oxidation of the phosphine to the phosphine oxide.

Following oxidation with hydrogen peroxide, the solvents (water and isopropanol) are removed from the reaction product by heating to 65° C. under vacuum. The resulting viscous syrup weighs 510 g. The product has the following analyses: C61.64, 61.53; H8.43, 8.15; P11.30, 11.42; N7.35, 7.49.

This is an effective flame retardant when added to polyphenylene oxide compositions in amounts of 4 to 15 parts per hundred.

TEST PROCEDURES

FLAME RETARDANCY TESTS

The oxygen index test (ASTM D-2863) employs a vertical glass tube 60 cm high and 8.4 cm in diameter in which a rod or strip specimen is held vertically by a clamp at its bottom end. A mixture of oxygen and nitrogen is metered into the bottom of the tube, passed through a bed of glass beads at the bottom to smooth the flow of gas. The sample is ignited at its upper end with a hydrogen flame, which is then withdrawn, and the sample burns like a candle from the top down. The atmosphere that permits steady burning is determined. The limiting oxygen index or simply oxygen index is the minimum fraction of oxygen in an oxygen-nitrogen mixture which will just sustain burning for two inches or three minutes, whichever comes first.

In the Underwriters Laboratory (UL)-Subject 94 vertical burn test, a sample (5.0×0.5 in.) is exposed vertically to a Bunsen burner flame for 10 seconds. The sample is ignited at the bottom and burns up. If the specimen self-extinguishes within 30 seconds, another 10 second application is made. Flaming droplets are allowed to fall on dry absorbent surgical cotton located 12 inches below the sample. If the average burning time for ten samples is less than 5 seconds and the drips do not ignite the cotton, the material is classified 94V-0. If the time is less than 25 seconds and the drips do not ignite the cotton, the material is classified 94V-1. If the sample is self-extinguishing but the cotton is ignited, the material is classified as 94V-2.

STRESS CRACKING TEST

The specimens (Noryl ®) used in the stress cracking test are injection molded. The dimensions are 2.5"×0.5"×0.125". The Noryl bar is bent and placed in the stress jig to give approximately 1% strain. Liquid plasticizer or flame retardant to be evaluated is brushed over the middle 0.5" of the bar. Time to first visible crack and complete failure of the bar are recorded. The test is performed at room or elevated temperature.

SPIRAL FLOW PROCEDURE

Evaluation of plastic flow for comparison purposes is done using an injection molding machine and spiral flow mold. The mold consists of a cavity in the shape of a spiral in which flow or distance numbers in inches are inscribed in the cavity. Molten plastic enters the cavity and fills the mold's cavity. Depending on the flow characteristic of the plastic resin, the spiral will fill up more (better flow) or less (poorer flow). The flow also depends on molding profile (injection temperatures, pressures, shot size, etc.), therefore comparison of different resins are done at the same conditions. The reading of the flow is simply done by removing the molded spiral and reading off the number of inches it flows.

EXTRUSION COMPOUNDING

To compound resin and additives, first a dry blend of the powdered resin and liquid or solid additive is prepared. The dry blend is then fed into the twin screw extruder at preselected temperature. The resin and additives are melt compounded inside the extruder where the temperature and mixing screw plasticate and mix the ingredients. The molten compound exits through a nozzle and immediately enters a cooling bath (water) and then chopped to give pellets.

Reference is now made to the Table showing the physical characteristics of an exemplary compound of the invention (CODPPO) compared to known flame retardants. It will be noted that the CODPPO not only did not stress crack but, unlike other candidate compounds, gave very good moldings.

TABLE I

STRESS CRACK RESISTANCE AND FLAME RETARDANCY TESTS OF NORYL ®* RESIN

| Flame Retardant | Concentration (phr) | Time To Stress Crack | Oxygen Index | UL-94 (sec.) | Spiral Flow (in.) | Comments |
| --- | --- | --- | --- | --- | --- | --- |
| K-50 | 12 | 15 min. | 29.7 | 7 | 37 | Juices |
| MXP | 12 | 130 hrs. | — | 6.2 | 35.5 | — |
| BHPPO | 8 | ** | 27.9 | 9.5 | — | Gases |
| K-50/BHPPO | 8/3 | 15 min. | 28 | 7 | 33 | Good molding |
| TPPO | 8 | solid | 30.3 | 8.8 | — | — |
|  | 12 | solid | 31.2 | 5.3 | — | — |
| TOPO | 12 | solid | 28.8 | 14.6 | — | Too volatile |
| HODPO | — | 2 hrs. | — | — | — | — |
| PABPO | 8 | ** | 29.1 | 9.6 | — | Gases |
|  | 12 | — | 29.7 | 7.6 | — | — |
| CODPPO | 7.1 | ** | 29.5 | 6.5 | 35 | Very good |
|  | 12 | ** | 30 | 4.1 | — | moldings |

TPPO — triphenyl phosphine oxide
TOPO — trioctyl phosphine oxide
HODPO — hexyl octyl decyl phosphine oxide
PABPO — phenyl allyl ether bishydroxypropyl phosphine oxide
CODPPO — cyclooctyl hydroxypropyl phosphine oxide from cyclooctadiene and allyl alcohol
K-50 — Kronitex 50 ®; a triphenyl phosphate having about 0.33 mole percent isopropyl groups
MXP — mixed mesityl xylyl phosphate ester
BHPPO — butyl bis(3-hydroxypropyl)phosphine oxide
* — The trademark for polyphenylene oxide (PPO) modified with impact polystyrene (PS) resin (40 PPO/60 PS), produced and sold by the General Electric Company
** — does not stress crack

What is claimed is:

1. A cyclic phosphine oxide composition containing the grouping:

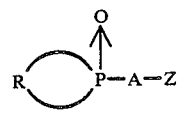

wherein P is phosphorus, O is oxygen, A is an alkylene chain of 2 to 12 carbon atoms, Z is a polar group and R represents the carbon atoms in a phosphorus-containing ring formed by alkylating an ethylenically unsaturated cyclic hydrocarbon with phosphine.

2. The composition of claim 1 wherein Z is selected from the class consisting of amino, hydroxy, amide, cyano, carboxylic acid and esters thereof and sulfonic acid and esters thereof.

3. The composition of claim 2 wherein the cyclic hydrocarbon is selected from the class consisting of cyclooctadiene, cyclodecadiene and cyclododecatriene.

4. A cyclic phosphine oxide of the formula:

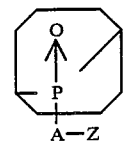

wherein A and Z have the meaning aforesaid.

5. The cyclic phosphine oxide of the formula:

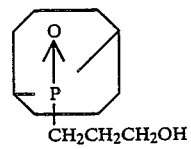

6. The cyclic phosphine oxide of the formula:

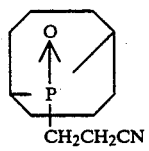
CH₂CH₂CN

7. A flame retardant styrene modified polyphenylene ether resin having as a flame retardant therefor, a cyclic phosphine oxide composition containing the grouping:

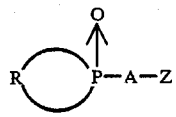

wherein P is phosphorus, O is oxygen, A is an alkylene chain of 2 to 12 carbon atoms, Z is a polar group and R represents the carbon atoms in a phosphorus-containing ring formed by alkylating an ethylenically unsaturated cyclic hydrocarbon.

8. The flame retardant resin of claim 7 wherein Z is selected from the class consisting of amino, hydroxy, amide, cyano, carboxylic acid and esters thereof and sulfonic acid and esters thereof.

9. The flame retardant resin of claim 8 wherein the cyclic hydrocarbon is selected from the class consisting of cyclooctadiene, cyclodecadiene and cyclododecatriene.

10. A flame retardant styrene modified polyphenylene ether resin containing as a flame retardant the compound:

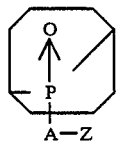
A—Z wherein A and Z have the meaning aforesaid.

11. A flame retardant styrene modified polyphenylene ether resin containing as a flame retardant the compound:

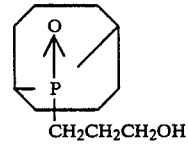
CH₂CH₂CH₂OH

12. A flame retardant styrene modified polyphenylene ether resin containing as a flame retardant the compound:

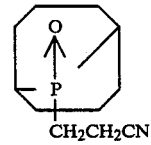
CH₂CH₂CN

13. A cyclic phosphine oxide composition produced by the steps of:
 (1) alkylating phosphine with an ethylenically unsaturated cyclic hydrocarbon to form a cyclic phosphine reaction product having free hydrogens attached to the phosphorus atom,
 (2) further alkylating the cyclic phosphine reaction product of (1) with a 1-alkene having at least one polar group, and
 (3) oxidizing the alkylated cyclic phosphine of step (2).

14. The composition of claim 13 in which the polar group of the 1-alkene in step (2) is attached to the terminal carbon atom.

15. The composition of claim 14 in which the ethylenically unsaturated cyclic hydrocarbon is cyclooctadiene and the polar group is selected from the class consisting of amino, hydroxy, amide, cyano, carboxylic acid and esters thereof and sulfonic acid and esters thereof.

16. The composition of claim 14 in which the 1-alkene is allyl alcohol.

17. The composition of claim 14 in which the alkene is acrylonitrile.

18. A flame retardant styrene modified polyphenylene ether resin having as a flame retardant therefor, any of the cyclic phosphate oxides of claims 13, 14, 15, 16 or 17.

* * * * *